United States Patent
Bor

(10) Patent No.: US 8,663,208 B2
(45) Date of Patent: Mar. 4, 2014

(54) SYSTEM AND METHOD FOR INTRASTROMAL REFRACTIVE CORRECTION

(75) Inventor: Zsolt Bor, San Clemente, CA (US)

(73) Assignee: AMO Development, LLC, Santa Ana, CA (US)

(*) Notice: Subject to any disclaimer, the term of this patent is extended or adjusted under 35 U.S.C. 154(b) by 455 days.

(21) Appl. No.: 12/703,014

(22) Filed: Feb. 9, 2010

(65) Prior Publication Data

US 2011/0040293 A1     Feb. 17, 2011

Related U.S. Application Data

(60) Provisional application No. 61/151,160, filed on Feb. 9, 2009.

(51) Int. Cl.
*A61B 18/18* (2006.01)

(52) U.S. Cl.
USPC .................................................. 606/5

(58) Field of Classification Search
USPC .................................................. 606/5
See application file for complete search history.

(56) References Cited

U.S. PATENT DOCUMENTS

| | | | |
|---|---|---|---|
| 4,665,913 A * | 5/1987 | L'Esperance, Jr. | 606/3 |
| 4,669,466 A * | 6/1987 | L'Esperance | 606/3 |
| 4,764,930 A | 8/1988 | Bille et al. | |
| 4,823,801 A * | 4/1989 | Sakane | 600/452 |
| 4,988,348 A | 1/1991 | Bille | |
| 5,533,997 A | 7/1996 | Ruiz | |
| 5,549,632 A | 8/1996 | Lai | |
| 5,807,381 A * | 9/1998 | Lieberman | 606/5 |
| 5,928,129 A | 7/1999 | Ruiz | |
| 5,993,438 A | 11/1999 | Juhasz et al. | |
| 6,280,435 B1 | 8/2001 | Odrich et al. | |
| 6,325,792 B1 | 12/2001 | Swinger et al. | |
| 6,342,053 B1 * | 1/2002 | Berry | 606/5 |
| RE37,585 E | 3/2002 | Mourou et al. | |
| 6,451,006 B1 | 9/2002 | Bille | |
| 6,610,051 B2 | 8/2003 | Bille | |
| 6,648,877 B1 | 11/2003 | Juhasz et al. | |
| 6,663,619 B2 | 12/2003 | Odrich et al. | |
| 6,740,078 B2 | 5/2004 | Tamayo | |
| 6,969,386 B2 | 11/2005 | Tamayo et al. | |
| 7,044,602 B2 | 5/2006 | Chernyak | |
| 7,101,364 B2 | 9/2006 | Bille | |

(Continued)

FOREIGN PATENT DOCUMENTS

EP          209992 A1     1/1987

OTHER PUBLICATIONS

Office Action mailed Jul. 24, 2013 for European Application No. 10705474.4 filed Feb. 9, 2010.

*Primary Examiner* — Bill Thomson
*Assistant Examiner* — John R Downey
(74) *Attorney, Agent, or Firm* — AMO Development, LLC

(57) ABSTRACT

System and method of intrastromal refractive correction. The system includes a laser source operable to produce a pulsed beam, a scanner operable to direct the pulsed beam at the eye, and a controller coupled to the laser source and the scanner. The controller determines an intrastromal incision pattern based on a refractive condition of an eye, and directs the scanner to intrastromally incise the pattern in an applanated cornea with the pulsed beam. Following de-applanation, the cornea is reshaped in response to the intrastromal incision pattern to correct the refractive condition.

8 Claims, 14 Drawing Sheets

(56) References Cited

U.S. PATENT DOCUMENTS

| | | |
|---|---|---|
| 7,238,176 B2 | 7/2007 | Loesel et al. |
| 7,261,415 B2 | 8/2007 | Chernyak |
| 7,293,873 B2 | 11/2007 | Dai et al. |
| 7,717,907 B2 * | 5/2010 | Ruiz et al. .................. 606/5 |
| 7,887,532 B2 * | 2/2011 | Kurtz et al. .................. 606/5 |
| 2004/0243111 A1 | 12/2004 | Bendett et al. |
| 2005/0280777 A1 | 12/2005 | Dai |
| 2006/0017883 A1 | 1/2006 | Dai et al. |
| 2007/0106376 A1 | 5/2007 | Roberts et al. |
| 2008/0039825 A1 | 2/2008 | Lai |
| 2009/0157061 A1 | 6/2009 | Ruiz et al. |

\* cited by examiner

SYSTEM AND METHOD FOR INTRASTROMAL REFRACTIVE CORRECTION

CROSS-REFERENCE TO RELATED APPLICATION

This application claims the benefit of U.S. Provisional Application No. 61/151,160, filed Feb. 9, 2009.

BACKGROUND OF THE INVENTION

1. Field of the Invention

The field of the present invention is generally related to photoaltering materials and more particularly, to systems and methods for intrastromal refractive correction.

2. Background

Pulsed laser beams include bursts or pulses of light, as implied by name, and have been used for photoalteration of materials, both inorganic and organic alike. Typically, a pulsed laser beam is focused onto a desired area of the material to photoalter the material in this area and, in some instances, the associated peripheral area. Examples of photoalteration of the material include, but are not necessarily limited to, chemical and physical alterations, chemical and physical breakdown, disintegration, ablation, vaporization, or the like.

One example of photoalteration using pulsed laser beams is the photodisruption (e.g., via laser induced optical breakdown) of a material. Localized photodisruptions can be placed at or below the surface of the material to produce high-precision material processing. For example, a micro-optics scanning system may be used to scan the pulsed laser beams to produce an incision in the material and create a flap therefrom. The term "scan" or "scanning" refers to the movement of the focal point of the pulsed laser beam along a desired path or in a desired pattern. To create a flap of the material, the pulsed laser beam is typically scanned along a region within the material at a pre-determined scan rate and with a pre-determined focal spot size. These flaps have been used to expose corneal tissue for refractive correction procedures, such as laser assisted in-situ keratomilieusis (LASIK).

More recently, corrective ophthalmic procedures addressing presbyopia, astigmatism, and other refractive conditions of the eye have gained interest. Intraocular lenses and intracorneal lenses have been designed for implant into the eye to provide some refractive correction. For example, accommodating intraocular lenses have been designed for implant into the capsular bag to provide some correction of presbyopia. Implanting such lenses typically involve a relatively lengthy procedure (e.g., in comparison with a LASIK procedure).

Accordingly, it is desirable to provide systems and methods for correcting presbyopia, astigmatism, and other refractive conditions of the eye. More particularly, it is desirable to provide systems and methods for refractive correction that decrease procedure time. It is also desirable to provide systems and methods for correcting presbyopia, astigmatism, and other refractive conditions of the eye that are minimally invasive or that may be combined with other ophthalmic procedures. Additionally, other desirable features and characteristics of the present invention will become apparent from the subsequent detailed description and the appended claims, taken in conjunction with the accompanying drawings and the foregoing technical field and background.

SUMMARY OF THE INVENTION

The present invention is directed towards systems and methods of intrastromal refractive correction. The term "intrastromal" is referred to herein as within the stroma of a corresponding cornea. An incision pattern is selected to correct a predetermined refractive condition of the eye, the incision pattern is intrastromally incised, and the cornea reshapes in response to the incision pattern to correct the refractive condition. In one embodiment, a system is provided for altering a refractive condition of an eye having a cornea. The system includes a laser source operable to produce a pulsed beam, a scanner operable to direct the pulsed beam at the eye, and a controller coupled to the laser source and the scanner. The controller is configured to determine an intrastromal incision pattern based on the refractive condition and direct the scanner to intrastromally incise the pattern in an applanated cornea with the pulsed beam. Following de-applanation, the refractive condition is altered by the pattern intrastromally incised in the cornea.

In another embodiment, a method of altering a refractive condition of an eye is provided including determining an incision pattern based on the refractive condition, orienting the incision pattern with respect to the eye, contacting the cornea with a lens, directing a pulsed laser beam at the eye, intrastromally scanning the pulsed laser beam to produce the incision pattern in a stromal tissue of the eye, and removing the lens from the cornea.

In another embodiment, a system for correction of a refractive characteristic of an eye is provided. The system includes a scanner operable to direct a pulsed laser beam at the eye and a controller coupled to the scanner. The controller is configured to determine an incision pattern based on the refractive characteristic of the eye and a model refractive characteristic and direct the scanner to intrastromally incise the cornea with the pulsed laser beam to produce the incision pattern between the epithelium and the endothelium. The incision pattern includes a plurality of elements, and each of the elements is radially separated from one another based on a common alignment axis. The refractive characteristic of the eye is modified by the incision pattern to the model refractive characteristic.

BRIEF DESCRIPTION OF THE DRAWINGS

In the drawings, wherein like reference numerals refer to similar components.

DETAILED DESCRIPTION

The present invention provides systems and methods for intrastromal refractive correction of an eye. In one embodiment, an incision pattern having a single element or multiple elements is intrastromally incised in the cornea of the eye to reshape the eye by a predetermined displacement of the resulting tissue structure. In a preferred embodiment, all of the incisions of the incision pattern remain within the stroma, and the anterior corneal surface (e.g., epithelium) remains substantially intact (i.e, absent photoalteration of the anterior corneal surface from the intrastromal incisions). Each incision of the pattern separates the stromal tissue into at least two regions adjacent to the incision. Following incision of the pattern, the two regions corresponding to each incision tend to displace with respect to one another as a result of external or intrinsic biomechanical forces associated with the eye, release of pre-tensions (e.g., surface tension associated with the corneal epithelium), stresses, pressures (e.g., intraocular pressure), or the like. With one or more incisions, the combined displacement(s) associated with the incision pattern can be determined and selected or designed to correct refractive characteristics of the eye. The incision pattern may include one or more repeating elements and is preferably selected or designed to reshape the eye in a manner consistent with modifying a refractive characteristic of the eye to a predetermined model. With the systems and methods of the present invention, a variety of patterns may be intrastromally incised in a patient eye, and a variety of refractive corrections may be treated with one or more of such patterns. For example, the instrastromal incision pattern may be selected or designed to correct for presbyopia, myopia, an astigmatism, or the like. Other refractive corrections to the eye may be performed with the present invention.

Figure 1:
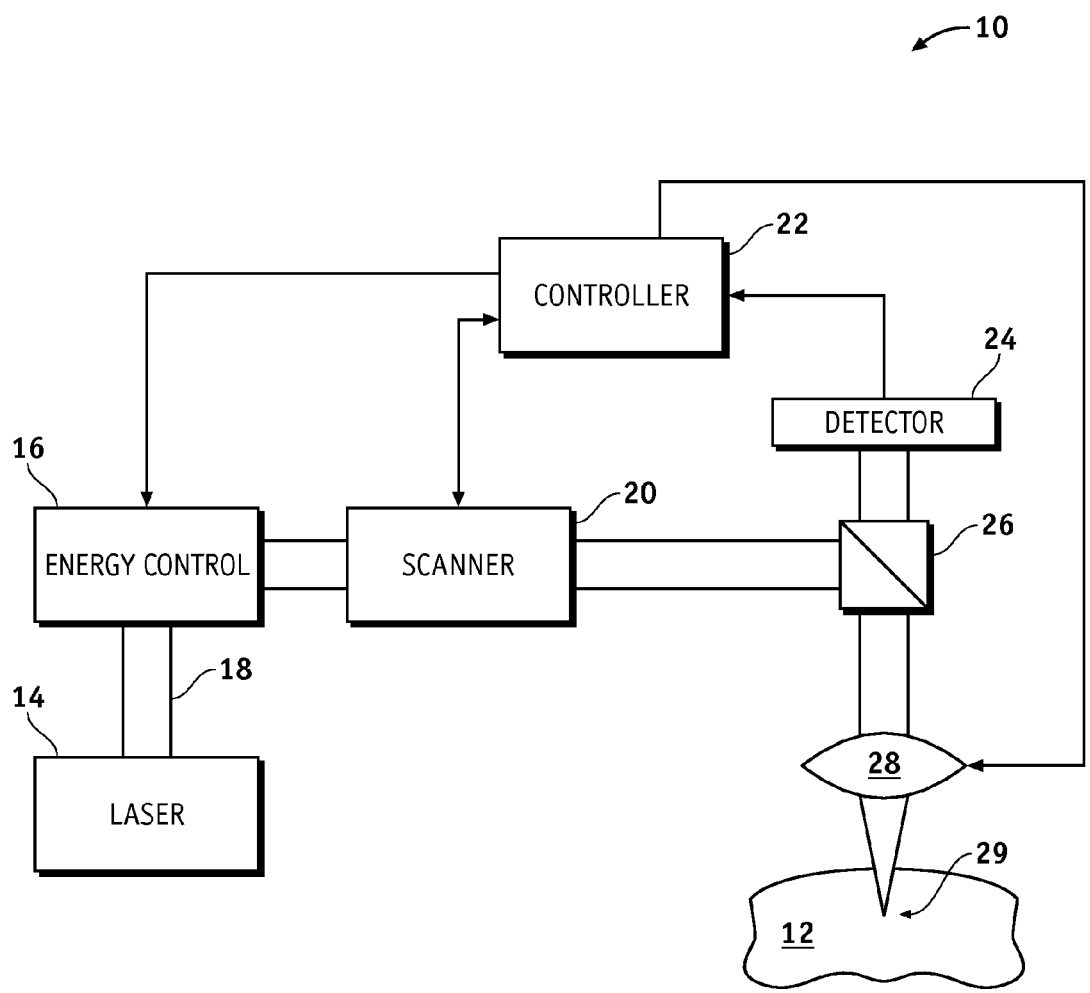
FIG. 1 is a block diagram of a laser system in accordance with one embodiment.

Referring to the drawings, a system 10 for intrastromal refractive correction of an eye 12 is shown in FIG. 1. The system 10 includes, but is not necessarily limited to, a laser source 14 capable of generating a pulsed laser beam 18, an energy control module 16 for varying the pulse energy of the pulsed laser beam 18, a scanner 20, a controller 22, and focusing optics 28 that direct a focal spot 30 of the pulsed laser beam 18 to a position within the stromal tissue of the eye 12 (e.g., sub-epithelium). The controller 22 (e.g., a processor operating suitable control software) communicates with the scanner 20 and/or the focusing optics 28 to control the direction of the focal spot 30 during scanning within the stromal tissue. An operator interface (not shown) may also be coupled with the controller 22 for initiation/selection of various system functions. In one embodiment, the interface facilitates operator selection of a particular incision pattern and various properties corresponding with the selected incision pattern. For example, the type of intrastromal incision (e.g., circular, oval, arc segment, linear segment, cylindrical, conical, or the like), number of incision elements, location of the incision element(s) within the cornea (e.g., maximum and minimum depth), incision angle (e.g., based on an optical axis associated with the eye, or the like, may be selected by the operator via the interface. Other functions of the system 10 may be controlled at least in part by the operator interface.

To impart at least a portion of the system control, software, firmware, or the like, can be used to command the actions and placement of the scanner 20 via a motion control system, such as a closed-loop proportional integral derivative (PID) control system or other control methodology. In this embodiment, the system 10 further includes a beam splitter 26 and a detector 24 coupled to the controller 22 to provide a feedback control mechanism for the pulsed laser beam 18. The beam splitter 26 and detector 24 may also be omitted in other embodiments, for example, with different control mechanisms.

The controller 22 includes computer hardware and/or software, often including one or more programmable processing units operable to execute machine readable program instructions or code for implementing some or all of one or more of the methods described herein. The code is often embodied in a tangible media such as a memory (optionally a read only memory, a random access memory, a non-volatile memory, or the like) and/or a recording media (such as a floppy disk, a hard drive, a CD, a DVD, a memory stick, or the like). The code and/or associated data and signals may also be transmitted to or from the controller 22 via a network connection (such as a wireless network, an Ethernet, an internet, an intranet, or the like) to the system 10, and some or all of the code may also be transmitted between components of the system 10 and/or within the controller 22 via one or more bus, and appropriate standard or proprietary communications cards, connectors, cables, and the like will often be included in the controller 22. The controller 22 is often configured to perform the calculations and signal transmission steps described herein at least in part by programming the controller with the software code, which may be written as a single program, a series of separate subroutines or related programs, or the like. The controller 22 may include standard or proprietary digital and/or analog signal processing hardware, software, and/or firmware, and will typically have sufficient processing power to perform the calculations described herein during treatment of the patient. The controller 22 optionally includes a personal computer, a notebook computer, a tablet computer, a proprietary processing unit, or a combination thereof. Standard or proprietary input devices (such as a mouse, keyboard, touchscreen, joystick, etc.) and output devices (such as a printer, speakers, display, etc.) associated with computer systems may also be included, and processors having a plurality of processing units (or even separate computers) may be employed in a wide range of centralized or distributed data processing architectures.

In one embodiment, a database of intrastromal incision patterns are stored in a memory accessible by the controller 22, within the controller 22, or using a combination thereof. These patterns may be designed based on information pertaining to corneal re-shaping in response to a variety of factors (e.g., patient age, corneal characteristics, pre-procedure refractive conditions associated with the patient, or the like). This information may also be historically observed and accumulated from one or more patients or patient populations. Using operator input or controller 22 selection based on operator specified criteria (e.g., associated with the patient), an intrastromal incision pattern suitable to effect a desired corneal re-shaping (e.g., for presbyopia correction, astigmatism correction, or the like) is retrieved from the database. This pattern may also be modified by the operator (e.g., physician) to customize the pattern. For example, one or more parameters associated with the retrieved intrastromal incision pattern may be modified by operator input. Additionally, the pattern may be wholly specified by the operator apart from the patterns stored in the database. Some examples of parameters associated with the intrastromal incision patterns are described in greater detail hereinafter, though other parameters may be included. In another embodiment, one or more of the parameters of the intrastromal incision patterns are input by the operator and used in combination with default values of other parameters. The database can also be periodically updated, such as by a network connection to a central database, system software upgrades, or the like.

Movement of the focal point 29 of the pulsed laser beam 18 is accomplished via the scanner 20 in response to the controller 22. In one embodiment, the scanner 20 scans the pulsed laser beam 18 to intrastromally incise the cornea. To provide the pulsed laser beam 18, a chirped pulse laser amplification system, such as described in U.S. Pat. No. RE37,585, may be used for photoalteration. U.S. Pat. Publication No. 2004/0243111 also describes other methods of photoalteration, the entire disclosures of which are incorporated herein. Other devices or systems may be used to generate pulsed laser beams. For example, non-ultraviolet (UV), ultrashort pulsed laser technology can produce pulsed laser beams having pulse durations measured in femtoseconds. Some of the non-UV, ultrashort pulsed laser technology may be used in ophthalmic applications. For example, U.S. Pat. No. 5,993,438 discloses a device for performing ophthalmic surgical procedures to effect high-accuracy corrections of optical aberrations. U.S. Pat. No. 5,993,438, the entire disclosure of which is incorporated herein, discloses an intrastromal photodisruption technique for reshaping the cornea using a non-UV, ultrashort (e.g., femtosecond pulse duration), pulsed laser beam that propagates through corneal tissue and is focused at a point below the surface of the cornea to photodisrupt stromal tissue at the focal spot. The pulsed laser beam 18 is preferably linearly polarized, but may be configured in a different polarization state (e.g., circularly polarized). The focusing optics 28 direct the pulsed laser beam 18 toward the eye (e.g., into the cornea) for plasma mediated (e.g., non-UV) intrastromal photodisruption of tissue.

The system 10 is capable of generating the pulsed laser beam 18 with physical characteristics similar to those of the laser beams generated by a laser system disclosed in U.S. Pat. No. 4,764,930, the entire disclosure of which is incorporated herein, U.S. Pat. No. 5,993,438, or the like. For example, the system 10 can produce a non-UV, ultrashort pulsed laser beam for use as an incising laser beam. This pulsed laser beam preferably has laser pulses with durations as long as a few nanoseconds or as short as a few femtoseconds. For intrastromal photodisruption of the tissue, the pulsed laser beam 18 has a wavelength that permits the pulsed laser beam 18 to pass through the cornea without absorption by the corneal tissue. The wavelength of the pulsed laser beam 18 is generally in the range of about 3 µm to about 1.9 nm, and preferably between about 400 nm to about 3000 nm. For accomplishing photodisruption of stromal tissues at the focal spot, the irradiance of the pulsed laser beam 18 is preferably greater than the threshold for optical breakdown of the tissue. Although a non-UV, ultrashort pulsed laser beam is described in this embodiment, the pulsed laser beam 18 may have other pulse durations and different wavelengths in other embodiments.

Scanning is accomplished with the scanner 20 via the controller 22 by selectively moving the focal spot(s) 30 to produce a structured scan pattern (e.g., a raster pattern, arcs, linear segments, rings, cylinders, a spiral pattern, or the like) of scan spots. Operating the scanner 20 to scan this structured pattern is particularly useful for controlling the spacing between scan spots of the pattern. The step rate at which the focal spot 29 is moved is referred to herein as the scan rate. For example, the scanner 20 can operate at scan rates between about 10 kHz and about 400 kHz, or at any other desired scan rate. In one embodiment, the scanner 20 generally moves the focal spot of the pulsed laser beam 18 through the desired scan pattern at a substantially constant scan rate while maintaining a substantially constant separation between adjacent focal spots. Further details of laser scanners are known in the art, such as described, for example, in U.S. Pat. No. 5,549,632, the entire disclosure of which is incorporated herein by reference.

In one embodiment, the scanner 20 includes, but is not necessarily limited to, a pair of scanning mirrors or other optics to angularly deflect and scan one or more input beams (e.g, the pulsed laser beam 18). For example, scanning mirrors driven by galvanometers may be employed where each of the mirrors scans along different orthogonal axes (e.g., an x-axis and a y-axis). A focusing objective having one or more lenses can be used to image the input beam onto a focal plane of the system 10. The focal spot 29 may thus be scanned in two dimensions (e.g., along the x-axis and the y-axis) within the focal plane of the system 10. Scanning along the third dimension, i.e., moving the focal plane along an optical axis (e.g., a z-axis), may be achieved by moving the focusing objective, or one or more lenses within the focusing objective, along the optical axis.

For ophthalmic applications (e.g., corneal re-shaping for presbyopia correction, myopia mitigation, astigmatism correction, or the like), an incision pattern (e.g., substantially circular, oval, arcuate segments, linear segments, cylindrical, conical, or other shapes) may be scanned with a scan pattern based on the movement of the scanning mirrors. As the focal spot 29 is scanned within the corneal tissue, the pulsed laser beam 18 photoalters the intrastromal tissue. Using structured patterns, the distribution of scan spots is generally determined by the pulse frequency, the scan rate, and the amount of scan line separation. Generally, higher scan rates, enable shorter procedure times by increasing the rate at which corneal tissue can be photoaltered. For example, the scan rates may be selected from a range between about 30 MHz and about 1 GHz with a pulse width in a range between about 300 picoseconds and about 10 femtoseconds, although other scan rates and pulse widths may be used.

The system 10 may additionally acquire detailed information about optical aberrations to be corrected, at least in part, using the system 10. Examples of such detailed information include, but are not necessarily limited to, the extent of the desired correction, and the location in the cornea of the eye associated with the correction (e.g., where the correction can be made most effectively). The refractive power of the cornea may be used to indicate corrections. Wavefront analysis techniques, made possible by devices such as a Hartmann-Shack type sensor (not shown), can be used to generate maps of corneal refractive power. Other wavefront analysis techniques and sensors may also be used. The maps of corneal refractive power, or similar refractive power information provided by other means, such as corneal topographs or the like, can then be used to identify and locate the optical aberrations of the cornea that require correction. The intrastromal incision pattern may be selected to correct one or more of these optical aberrations.

A variety of techniques may be used to align the incision pattern with the eye and thus, align the refractive correction. In some embodiments, iris registration methodology associated with ablation procedures, such as used for LASIK, marking and/or fiducial techniques used with corneal flap creation, keratoplasty, and the like, and centration can be used to align the incision pattern with the eye. For example, U.S. Pat. Nos. 7,261,415 and 7,044,602, which are herein incorporated in entirety by reference, describe registration techniques to track the position of the eye. Additionally, the alignment reference may vary for different refractive corrections and be based on a variety of ocular features. For example, the alignment reference can be based on the pupil center, the iris boundary, and the like. In one embodiment, the alignment of the incision pattern accounts for pupil center shift, which may occur as a result of inconsistent iris actuation. The intrastromal incision patterns may also include elements with different references for orientation. For example, an intrastromal incision pattern may have multiple axes (e.g., dual or multiple centers) for orienting different elements.

In general, when the laser source 14 is activated, the focal spot 29 is selectively directed (e.g., via the scanner 20) along a beam path to photoalter stromal tissue. For example, the focal spot 29 is moved along a predetermined length and at a predetermined depth of the beam path. The pulsed laser beam 18 is then redirected through another location to scan along another beam path (e.g., from line-to-line, ring-to-ring, radial line to radial line, or the like) and the process of photoalteration is repeated. The sequence for directing the pulsed laser beam 18 through individually selected reference locations can be varied, and the extent of stromal tissue photoalteration while the incising laser beam is so directed, can be varied. Specifically, as indicated above, the amount of photoalteration can be based on the refractive power map. On the other hand, the sequence of reference areas that is followed during a customized procedure will depend on the particular objectives of the procedure.

Figure 2:
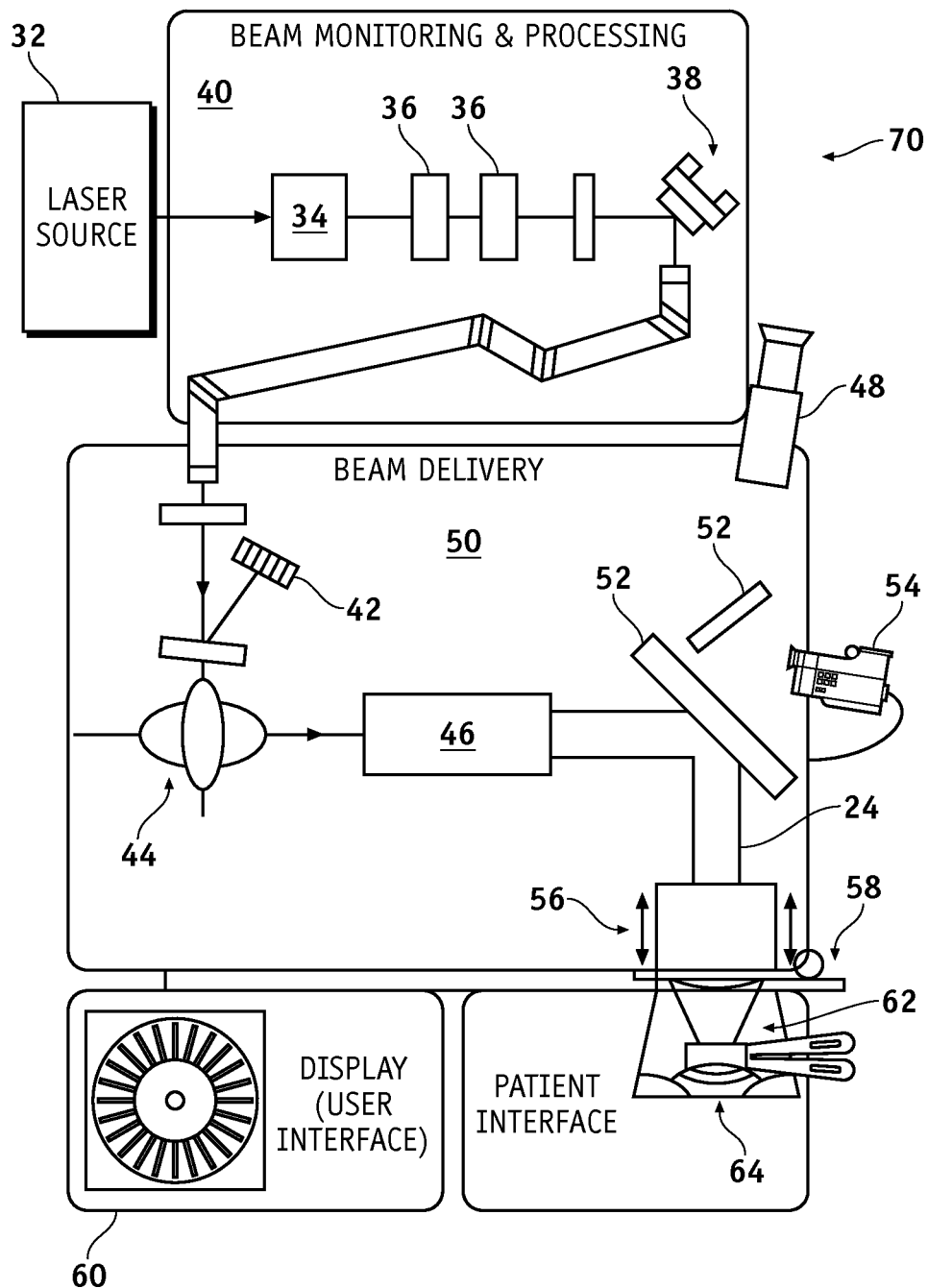
FIG. 2 is a block diagram of an ophthalmic laser system in accordance with another embodiment.

FIG. 2 is a block diagram of an ophthalmic laser system 30 in accordance with another embodiment, and the system 30 can be used for intrastromal refractive correction of the eye 12 shown in FIG. 1. In this embodiment, the system 30 includes, but is not necessarily limited to, a laser source 32 providing a pulsed laser beam, a beam monitoring and processing module 40, a beam delivery module 50, and a user interface 60 providing a display for viewing the eye 64 undergoing treatment by the system 30. The ophthalmic laser system 30 is coupled to an eye 64 via a patient interface 62, and the patient interface 62 may be coupled to the ophthalmic laser system 30 at a loading deck 58, for example. In this embodiment, the patient interface 62 assists with aligning the eye 64 to the beam delivery module 50 and utilizes an applanation surface (e.g., an applanation lens) to contact the corneal surface of the eye 64 to at least partially flatten the corneal surface prior to beam delivery. In operation, the pulsed laser beam is supplied to the beam monitoring and processing module 40 where the pulse energy, the focal spot separation, and the sub-surface depth of the pulsed laser beam are controlled. The beam delivery module 50 scans the pulsed laser beam along a desired scan region within the cornea of the eye 64 to intrastromally incise the pattern (i.e., in accordance with the selected and/or customized incision pattern) and thus, following withdrawal of the applanation surface, effect the desired refractive correction associated with the incision pattern.

In this embodiment, the use of a substantially planar applanation lens during scanning is preferred for maximizing the post-procedure re-shaping of the cornea resulting from the intrastromally incised pattern. For example, application of the applanation surface of the patient interface 62 against the cornea exerts a force that may be resisted by the eye 64 at least in part by a variety of factors, including by way of example and not limitation, intraocular pressure contributors, biomechanical stresses/tensions associated with the corneal surface and/or physical structure of the cornea, and the like. After applanation is diminished or ceased (e.g., following intrastromal incision of the pattern by withdrawal of the applanation surface or patient interface 62 from the corneal surface), one or more of these factors can facilitate a dislocation of the corneal tissue at the incision site. For example, the corneal tissue associated with one side of the incision site tends to shift or displace with respect to the corneal tissue associated with the other side of the incision site. Thus, the incision pattern may be selected to leverage the expected or estimated dislocation of corneal tissue to produce a desired re-shaping of the cornea and thus the implement a desired refractive correction of the eye 64. Other ocular biomechanics may also be included to select or design a particular intrastromal incision pattern.

In other embodiments, a non-planar lens (e.g., a lens having a curved contact surface that is dissimilar from the corneal surface) may also be substituted for the planar applanation lens to contact the cornea. The non-planar lens is shaped to decrease the curvature associated with a portion of the corneal surface around a desired incision site. This decrease in curvature is preferably from about a 10% curvature decrease to approaching planar (e.g., approaching an infinite curvature), and more preferably from about a 20% curvature decrease to about 90% curvature decrease. By altering the anterior corneal surface with the non-planar lens during applanation, a predicted degree of corneal tissue dislocation at the incision site can be produced, thereby modifying the refractive characteristics of the cornea and thus, the eye. The non-planar lens may also be shaped to invert the curvature associated with the corneal surface around the desired incision site. Other devices having an applanation surface that at least partially transmits the pulsed laser beam therethrough may also be used in combination with the system 30 to decrease the curvature of the cornea around the desired incision site(s) prior to beam delivery.

The operating pulse energy and operating focal spot separation may be selected by the beam monitoring and processing module 40 (e.g., in response to a selected, customized, or otherwise predetermined incision pattern) or implemented by the module 40 in response to operator input (e.g., via the user interface 60). In one embodiment, the beam monitoring and processing module 40 includes, but is not necessarily limited to, an energy attenuator 34, one or more energy monitors 36, and an active beam positioning mirror 38. The pulsed laser beam is directed from the laser source 32 to the energy attenuator 34, then to the energy monitor 36, and then to the active beam positioning mirror 38. The active beam positioning mirror 38 directs the pulsed laser beam from the beam monitoring and processing module 40 to the beam delivery module 50. Using the energy attenuator 34 and energy monitor 36 (e.g., in a feedback configuration), the pulse energy of the pulsed laser beam may be varied to desired values. Additionally, the spatial separation of the focal spots associated with the pulsed laser beam (e.g., adjacent spots within a scan line or adjacents spots associated with adjacent scan lines) may be varied by the beam monitoring and processing module 40.

After determining the operating pulse energy and focal spot separation, the beam delivery module 50 scans the pulsed laser beam at the desired scan region (e.g., a sub-surface region of the eye 64, such as within the stroma) in accordance with intrastromal incision pattern. In one embodiment, the beam delivery module 50 includes, but is not necessarily limited to, a beam position monitor 42, an x-y scanner 44, a beam expander 46, one or more beam splitters 52, and a z-scanning objective 56. In this embodiment, an operating microscope 48 and a video camera 54 are additionally coupled with the beam delivery module 50 to enhance viewing of the eye 64.

The pulsed laser beam is received from the beam monitoring and processing module 40 by the x-y scanner 44 and directed to the beam expander 46, and the beam expander 46 directs the pulsed laser beam to the z-scanning objective via the beam splitter(s) 52. The z-scanning objective 56 can vary the focal spot depth of the pulsed laser beam.

The configuration of the ophthalmic laser system 30 may vary as well as the organization of the various components and sub-components of the ophthalmic laser system 30. For example, some sub-components of the beam delivery module 50 may be incorporated with the beam monitoring and processing module 40 and vice versa.

As previously mentioned with respect to the various exemplary embodiments herein, following the intrastromal refractive correction procedure, the cornea is reshaped in accordance with the desired effect of the intrastromal incision pattern. In some embodiments, this results in a corneal shape well-suited to presbyopia correction. Some examples of corneal shapes include those desirable in conventional photoablation techniques that correct for presbyopia. A variety of other corneal shapes, whether conventional or to be developed in the future, may also be implemented using the intrastromal incision technique described in accordance with the present invention (e.g., as shown and described with respect to the systems 10, 30 and methods described herein and various other embodiments thereof). For example, U.S. Pat. Nos. 6,740,078 and 6,969,386 to Tamayo, U.S. Pat. Nos. 6,280,435 and 6,663,619 to Odrich, U.S. Pat. Nos. 5,928,129 and 5,533,997 to Ruiz, and U.S. Pat. No. 7,293,873 and U.S. Pub. Nos. 200502704, 20050280777, and 20060017883 to Dai, all of which are incorporated in entirety by reference herein, describe inter alia various ablation techniques to reshape the cornea for presbyopia correction. Each of these presbyopia correcting corneal shapes may be implemented with the systems 10, 30 and methods described herein.

Figure 3:
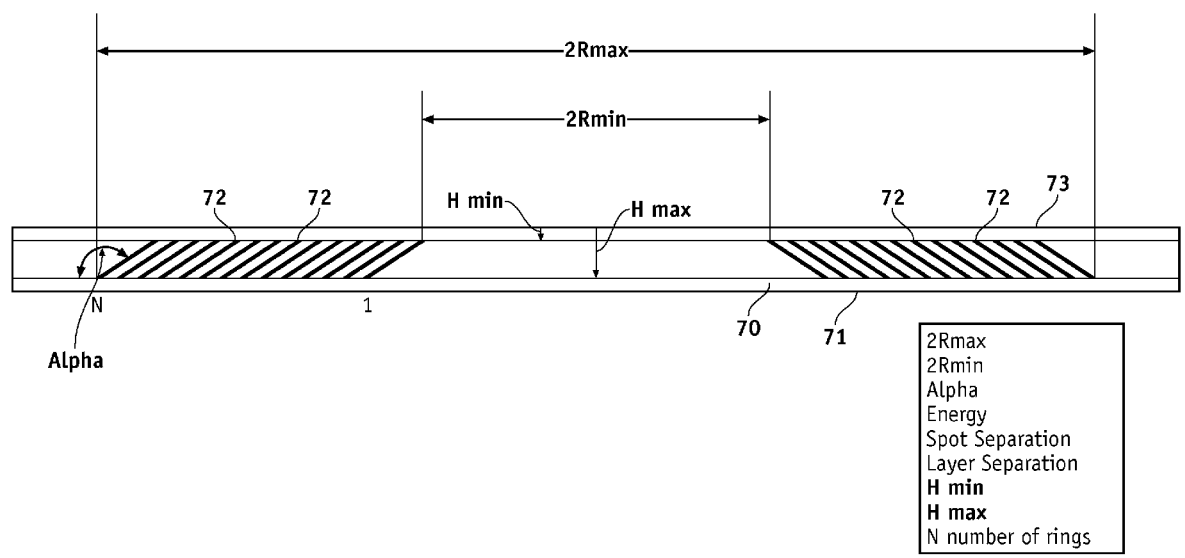
FIG. 3 is a cross-sectional view of an intrastromal incision pattern in accordance with one embodiment.
Figure 4:
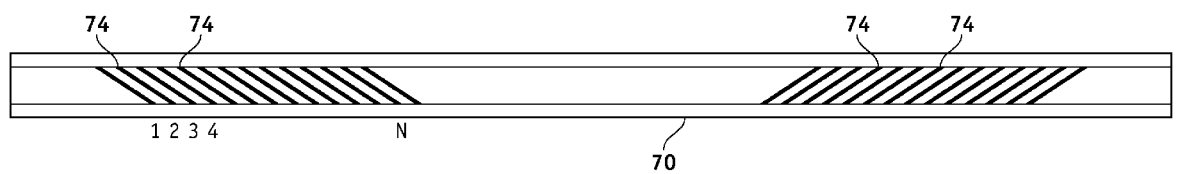
FIG. 4 is a cross-sectional view of an intrastromal incision pattern in accordance with another embodiment.

FIG. 3 is a cross-sectional view of an intrastromal incision pattern in corneal tissue 70 in accordance with one embodiment, and FIG. 4 is a cross-sectional view of an intrastromal incision pattern in corneal tissue 70 in accordance with another embodiment. For ease of discussion relating to the intrastromal incision pattern orientation, the representation of the corneal tissue 70 is shown in a planar or flattened condition, such as during applanation of the cornea (e.g., via the patient interface 62 shown in FIG. 2).

The intrastromal incision pattern includes one or more incisions formed by the pulsed laser beam (e.g., via photodisruption of the intrastromal tissue). Each incision may also be formed using one or more scan lines. For example, the pulsed laser beam can be scanned to form multiple scan lines having adjacent scan lines within a predetermined proximity that is sufficient to create an incision with desired characteristics (e.g., length, width, thickness, orientation within the stroma, and the like).

Some parameters of the intrastromal incision patterns include, but are not necessarily limited to, a minimum distance (H min) of the incision pattern from an anterior surface 73 of the corneal tissue 70, a maximum distance of the incision pattern from the anterior surface 73 (H max), a number (N) of incisions in the incision pattern, a maximum diameter (2Rmax) of the incision pattern, a minimum diameter (2Rmin) of the incision pattern, and an angle (alpha) associated with the corneal tissue 70. In this embodiment, the angle (alpha) is shown as oriented with respect to the layer structure of the corneal tissue 70 (e.g., 0 degrees being substantially aligned with the layer of the corneal tissue 70). In general, the maximum diameter (2Rmax) is less than about 10 mm, the minimum diameter (2Rmin) is greater than about 2 mm, the angle (alpha) is from about 10° to about 170°, the minimum distance (H min) is about 50 microns, the maximum distance (H max) is about 50 microns above an endothelium 71 of the corneal tissue 70, and the incision number (N) is about 1-15. Additionally, the intrastromal incision pattern may use laser beam pulses with a spot separation from about 0.1 microns to about 10 microns (e.g., based on the center of adjacent spots in a scan line), a spot layer separation of about 2 microns to about 20 microns (e.g., based on the center of adjacent spots corresponding with adjacent spots in adjacent scan lines), and a pulse energy of about 0.01 µJ to about 1 µJ.

The pattern shown in FIG. 3 includes a group of ring incisions 72 intrastromally located in the corneal tissue 70 and having an angle (alpha) greater than 90°. To form each of the incisions 72, the pulsed laser beam can be scanned, for example, to form adjacent concentric scan circles with decreasing radii as the beam is scanned from the maximum distant (Hmax) to the minimum distance (Hmin). In another example, the pulsed laser beam can be scanned to form adjacent concentric scan circles with increasing radii as the beam is scanned from the minimum distance (Hmin) to the maximum distant (Hmax), for example. In general, a variety of scanning procedures may be used for each of the incision patterns, although some scanning procedures may be beneficially executed within less time than other scanning procedures for the same incision pattern. The pattern shown in FIG. 4 includes a group of ring incisions 74 intrastromally located in the corneal tissue 70 and having an angle (alpha) less than 90° (i.e., an axis perpendicular to the corneal tissue 70).

The incision pattern may take a variety of shapes. Some incision patterns include multiple incision elements or repeating incision elements, such as shown in FIGS. 3 and 4 with the ring incisions 72, 74, and the elements may differ from one another. For example, the incision elements may have varying thicknesses from one another or within the individual incision element. While the ring incisions 72, 74 have an angle (alpha), the profile or cross-section may be non-linear (e.g., zig-zagged, curved, and the like) while retaining a general orientation with the angle (alpha). For example, ring incisions with a zig-zagged cross-section may be selected to facilitate some displacement control (e.g., control the displacement of corneal tissue on one side of the incision with respect to the corneal tissue on the other side of the incision). In another embodiment, the incision pattern includes multiple annular incisions that are staggered from the annular incision proximal to the anterior surface 73 of the cornea 70 to the annular incision proximal to the endothelium 71 with respect to adjacent annular incisions, and the annular incisions have an increasing inner diameter from the annular incision proximal to the anterior surface 73 of the cornea 70 to the annular incision proximal to the endothelium 71 (e.g., following annular incisions proximal to a central axis on outward).

Figure 5:
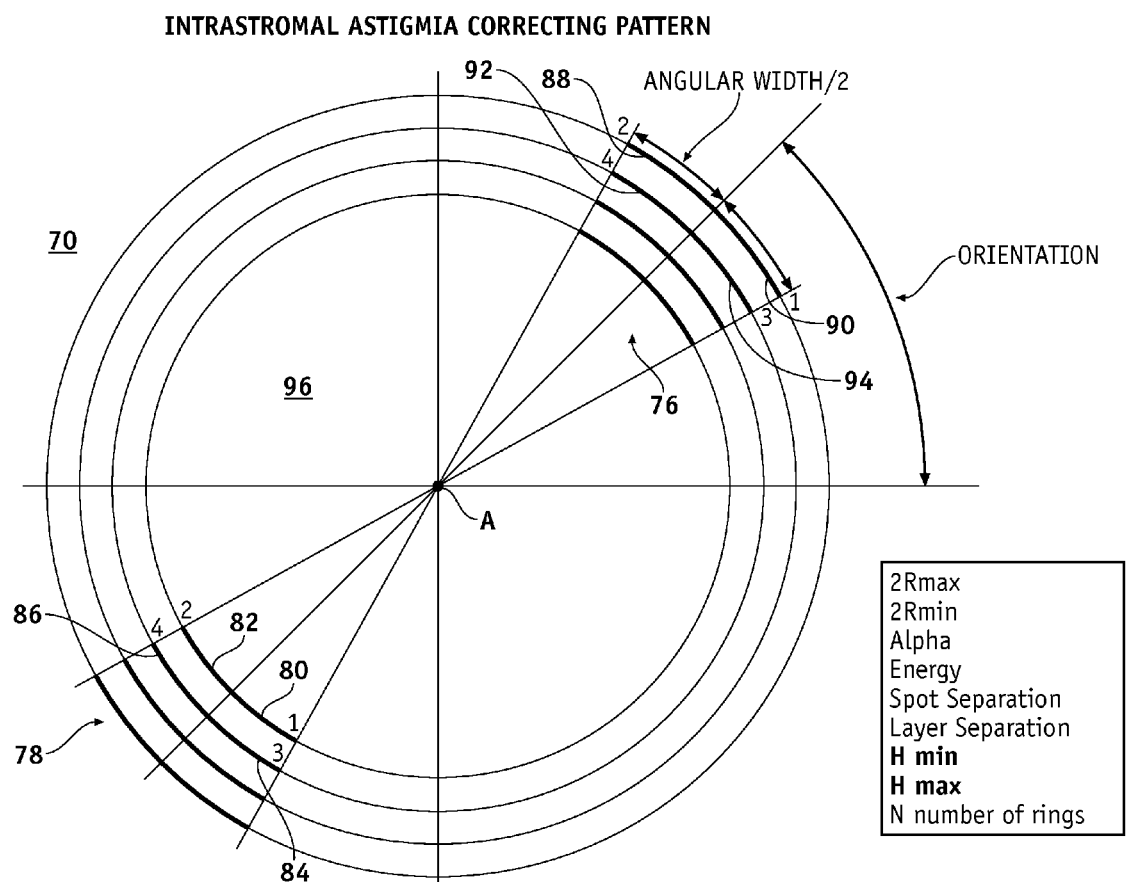
FIG. 5 is a top view of an intrastromal incision pattern in accordance with another embodiment.

FIG. 5 is a top view of an intrastromal incision pattern in accordance with another embodiment. The intrastromal incision pattern shown in FIG. 5 includes intrastromal incision arcs 80, 82, 84, 86, 88, 90, 92, 94 configured to correct an astigmatism. In this embodiment, the incision pattern is centered about an optical axis (A) in the corneal tissue 70 (e.g., such as a pupil center) and includes a first group 76 of incision arcs and a second group 78 of incision arcs that are both referenced to the optical axis (A). The nature and orientation of the astigmatism may be predetermined via wavefront analysis, as previously mentioned herein, and used to plan a desired refractive correction with the incision pattern. In one embodiment, the optical axis (A) is preferably determined based on the astigmatism data obtained via the wavefront analysis. Thus, the incision pattern correlates with the orientation of the astigmatism. Other aberration detection and ocular measurement systems or techniques may also be employed either alone or in combination with the wavefront analysis. For example, OCT may be used to map the cornea and correlated with the wavefront analysis to predict or model the corneal behavior for a selected incision pattern.

In this embodiment, the first group 76 includes incision arcs that are positioned based on an orientation angle with respect to a horizontal axis, and the second group 78 includes incision arcs that are positioned based on an orientation angle that is in an opposite direction as the orientation angle associated with the first group 76 (e.g., about 180° from the orientation angle associated with the first group 76). An angular width may be specified for forming the incision arcs about the orientation angle. For example, the first group 76 includes incision arcs 88, 90, 92, 94 that are bisected by the orientation angle such that the incisions arcs 88 and 92 have one half of the angular width and the incision arcs 90 and 94 have one half of the angular width, and the second group 78 includes incision arcs 80, 82, 84, 86 that are bisected by the orientation angle such that the incisions arcs 80 and 84 have one half of the angular width and the incision arcs 82 and 86 have one half of the angular width. Although the groups 76 and 78 are oriented in a symmetrically opposing configuration, the groups of incisions arcs in other embodiments may be oriented at a variety of angles about one or more central axes to effect a desired corneal reshaping and corresponding refractive correction.

Figure 6:
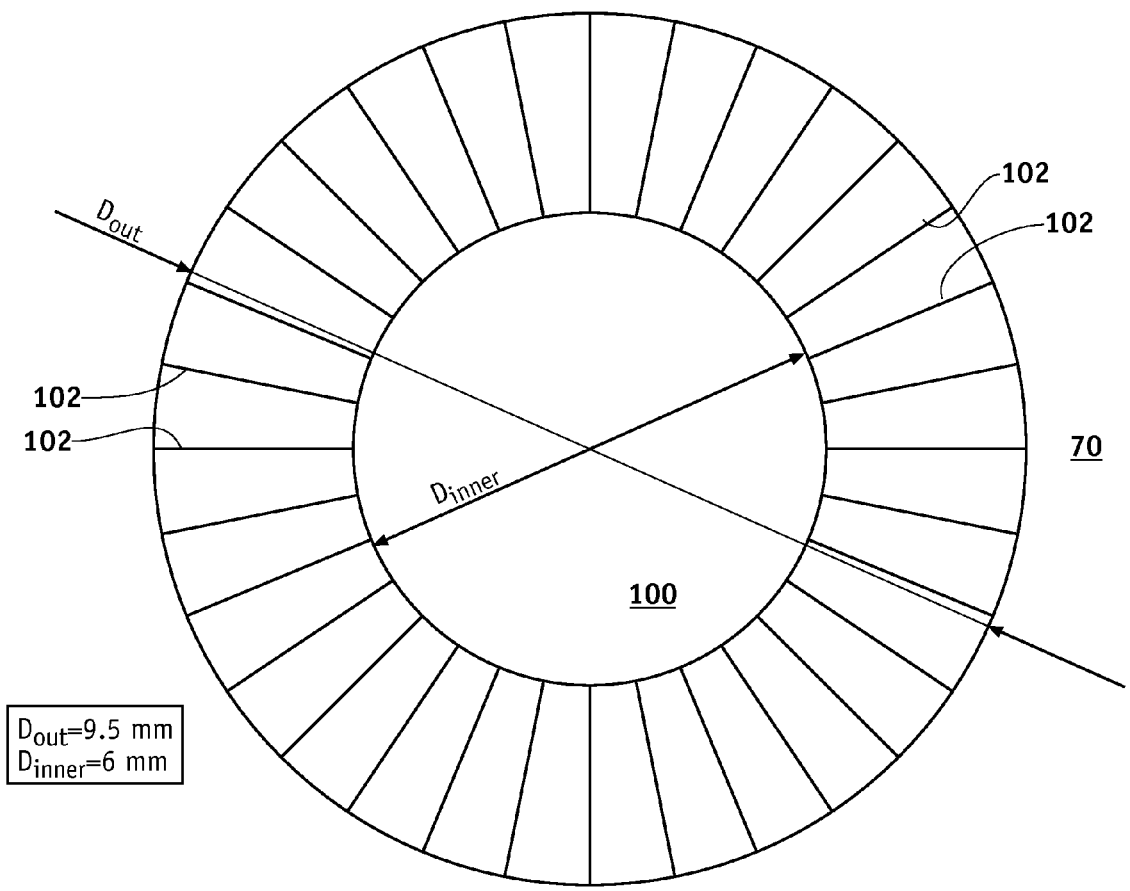
FIG. 6 is a top view of an intrastromal incision pattern in accordance with another embodiment.

FIG. 6 is a top view of an intrastromal incision pattern in accordance with another embodiment. The incision pattern shown in FIG. 6 includes intrastromal radial incisions 102 formed in the corneal tissue 70 and extending between an inner diameter ($D_{inner}$) and an outer diameter ($D_{out}$). In this embodiment, the incision pattern includes thirty-two radial incisions 102, the inner diameter ($D_{inner}$) is about 6 mm, and the outer diameter ($D_{out}$) is about 9.5 mm. Although the radial incisions 102 share a common inner and outer diameter, the inner and outer diameter may individually vary for one or more of the radial incisions 102. For presbyopia correction, the inner and outer diameters may be selected based on models utilizing a central zone and peripheral zone differentiation to effect a desired corneal shape, such as disclosed by U.S. Pat. Nos. 6,740,078, 6,969,386, 6,280,435, 6,663,619, 5,928,129, 5,533,997, and 7,293,873 and U.S. Pub. Nos. 200502704, 20050280777, and 20060017883, and the like.

Figure 7:
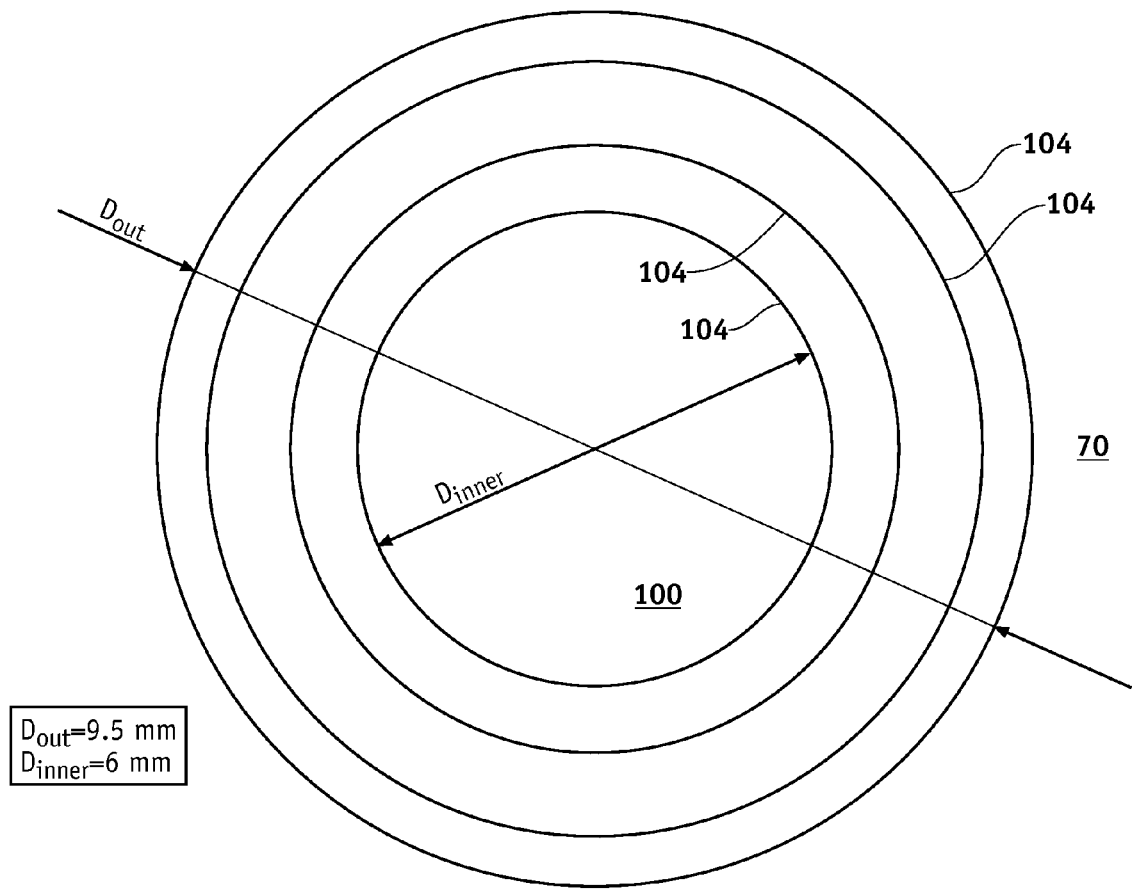
FIG. 7 is a top view of an intrastromal incision pattern in accordance with another embodiment.

FIG. 7 is a top view of an intrastromal incision pattern in accordance with another embodiment. The incision pattern shown in FIG. 7 includes intrastromal circular incisions 104 formed in the corneal tissue 70 and oriented between an inner diameter ($D_{inner}$) and an outer diameter ($D_{out}$). In this embodiment, the incision pattern includes four intrastromal circular incisions 104, the inner diameter ($D_{inner}$) is about 6 mm, and the outer diameter ($D_{out}$) is about 9.5 mm. The inner and outer diameter and the number of intrastromal circular incisions may vary in other embodiments. For presbyopia correction, the inner and outer diameters may be selected based on models utilizing a central zone and peripheral zone differentiation to effect a desired corneal shape, such as mentioned in connection with the intrastromal incision pattern shown in FIG. 6.

Figure 8:
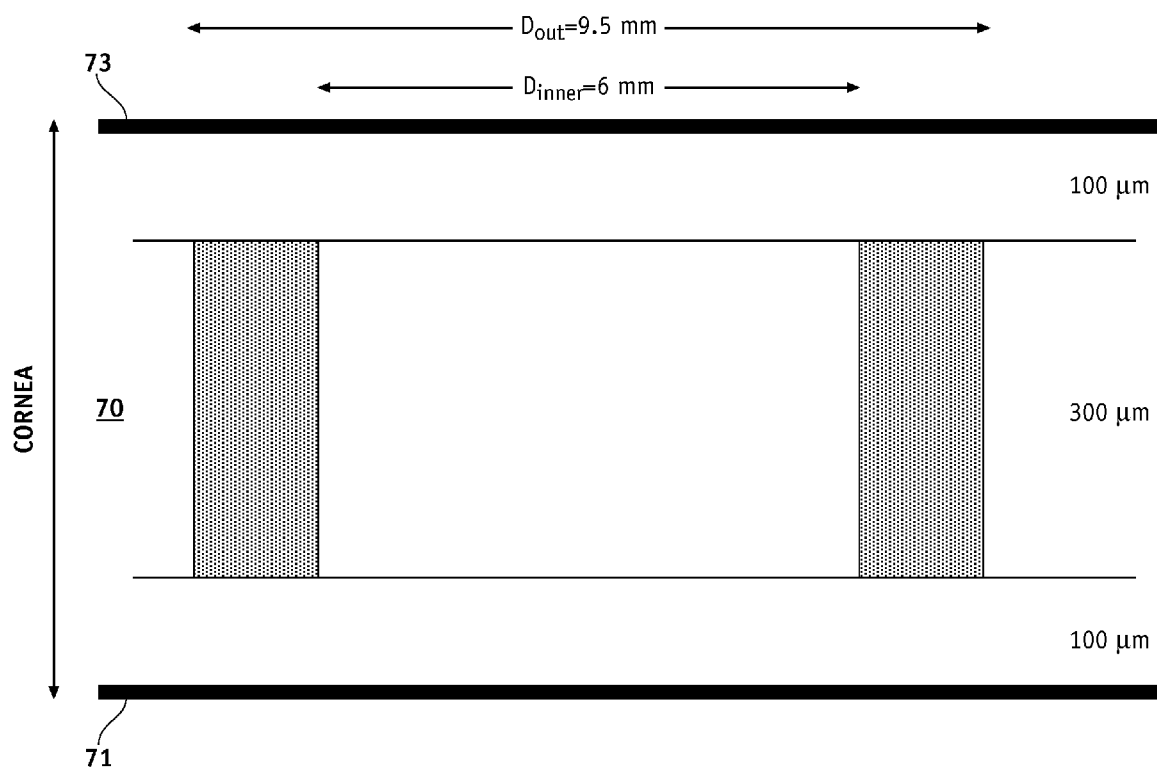
FIG. 8 is a cross-sectional view of an intrastromal incision pattern in accordance with one embodiment.

FIG. 8 is a cross-sectional view of an intrastromal incision pattern in accordance with another embodiment illustrating greater detail. The incision pattern shown in FIG. 8 includes an intrastromal incision formed in the corneal tissue 70 between the anterior surface 73 of the cornea 70 (e.g., the epithelium) and the endothelium 71. In this embodiment, the minimum distance (H min) of the intrastromal incision from the anterior surface 73 is about 100 μm, and the maximum distance (H max) of the intrastromal incision from the anterior surface 73 is about 100 μm. The intrastromal incision also has an inner diameter ($D_{inner}$) of about 6 mm and an outer diameter ($D_{out}$) of about 9.5 mm (e.g., a thickness of about 3.5 mm). For presbyopia correction, the inner and outer diameters may be selected based on models utilizing a central zone and peripheral zone differentiation to effect a desired corneal shape, such as mentioned in connection with the intrastromal incision pattern shown in FIGS. 6 and 7.

Figure 9:
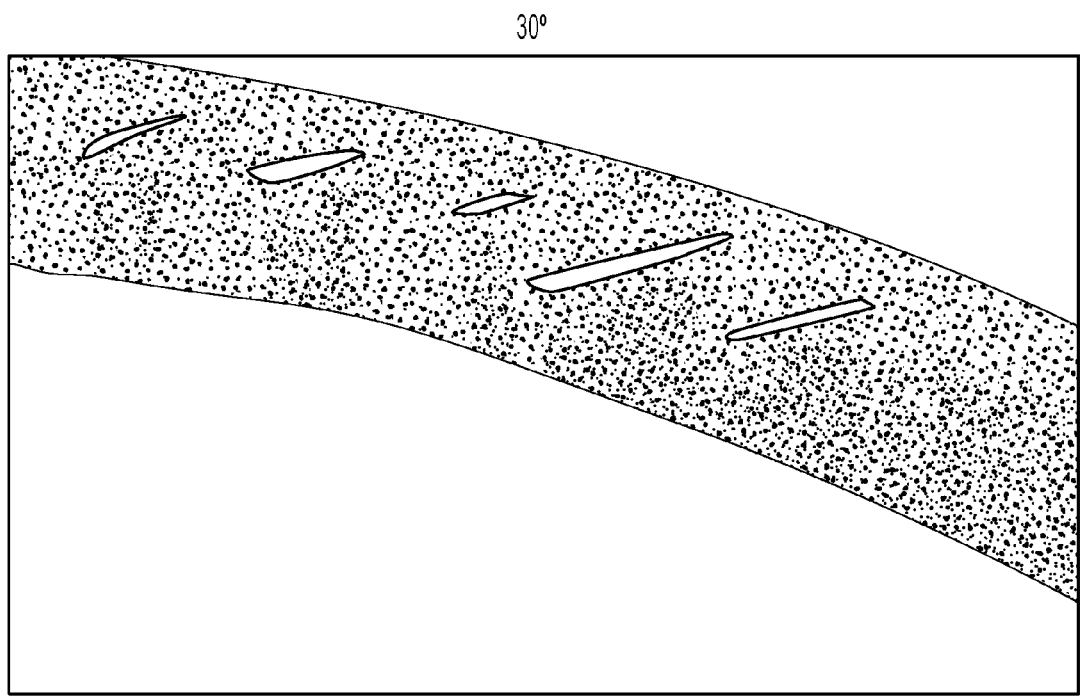
FIG. 9 is an optical coherence tomography (OCT) image illustrating an intrastromal incision pattern in accordance with one embodiment.
Figure 10:
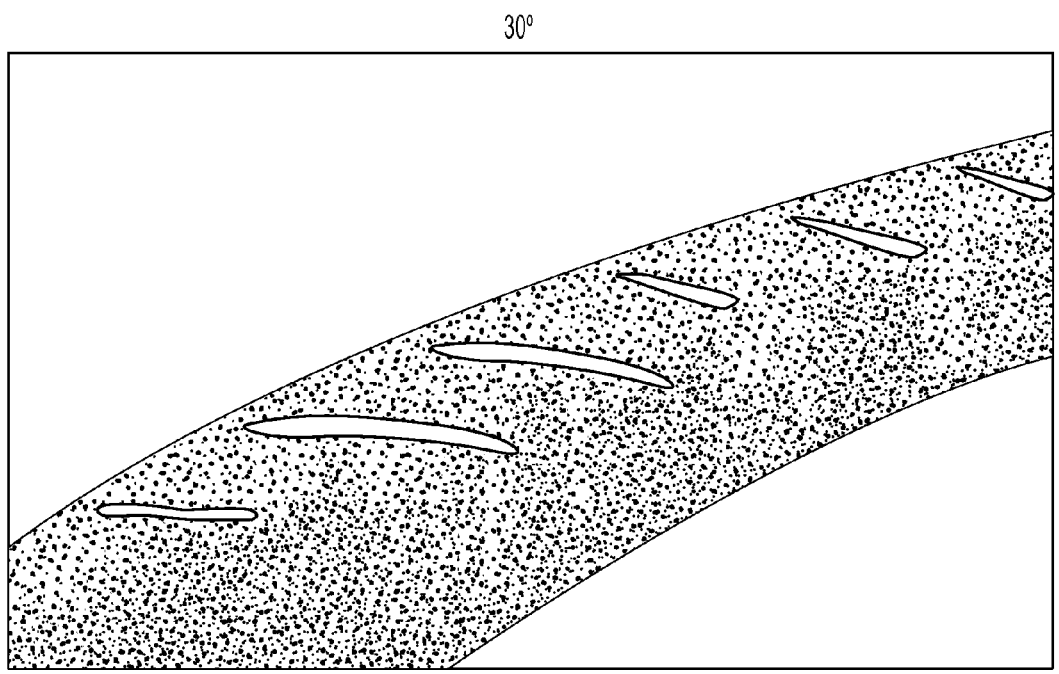
FIG. 10 is an OCT image illustrating an intrastromal incision pattern in accordance with another embodiment.
Figure 11:
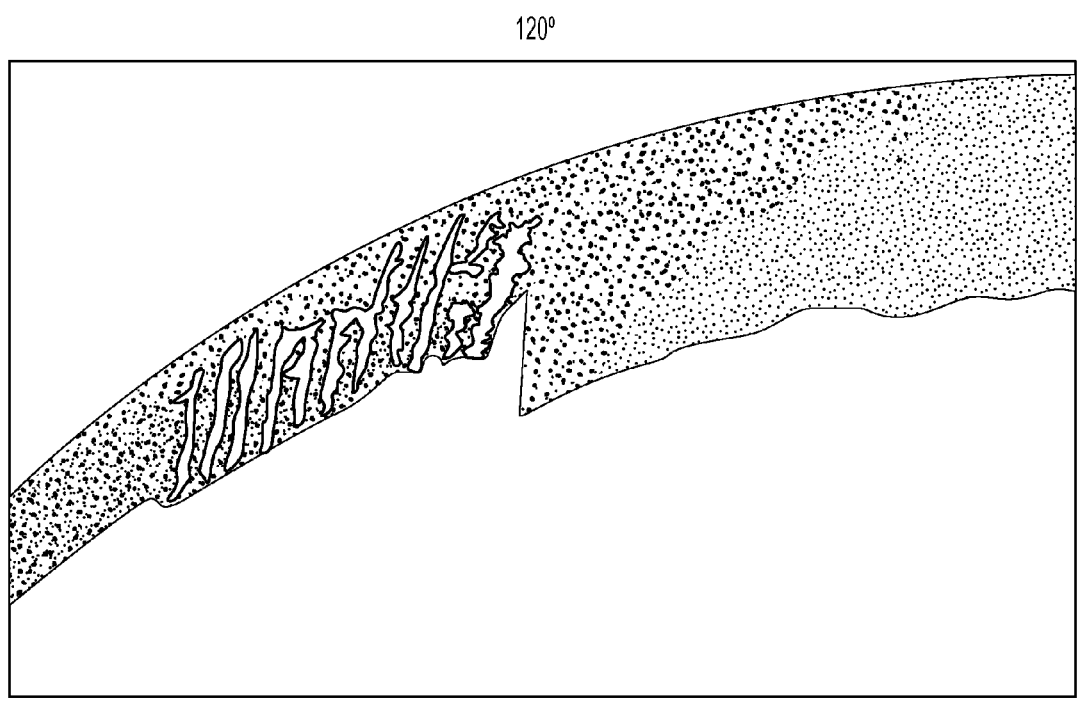
FIG. 11 is an OCT image illustrating an intrastromal incision pattern in accordance with another embodiment.
Figure 12:
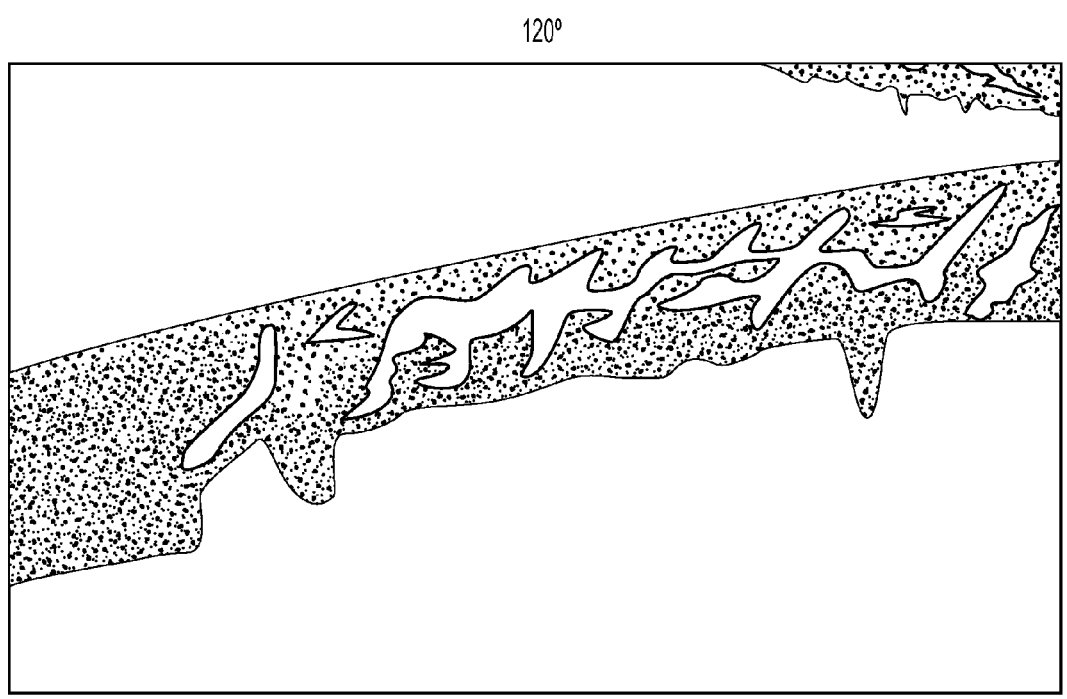
FIG. 12 is an OCT image illustrating an intrastromal incision pattern in accordance with another embodiment.
Figure 13:
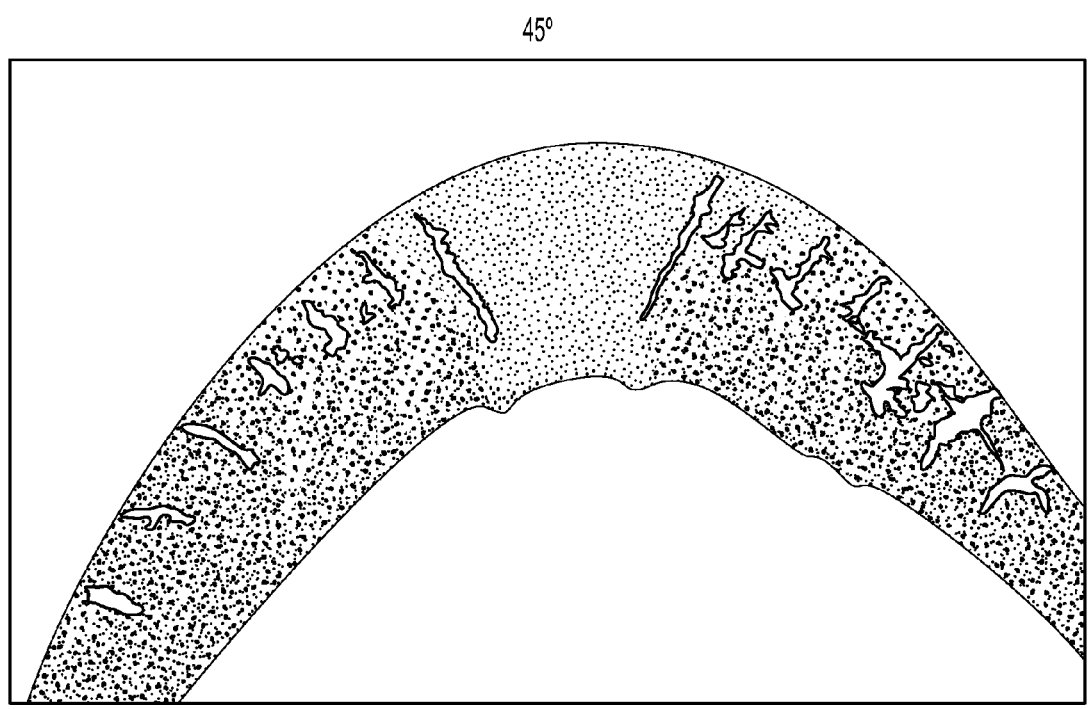
FIG. 13 is an OCT image illustrating an intrastromal incision pattern in accordance with another embodiment.
Figure 14:
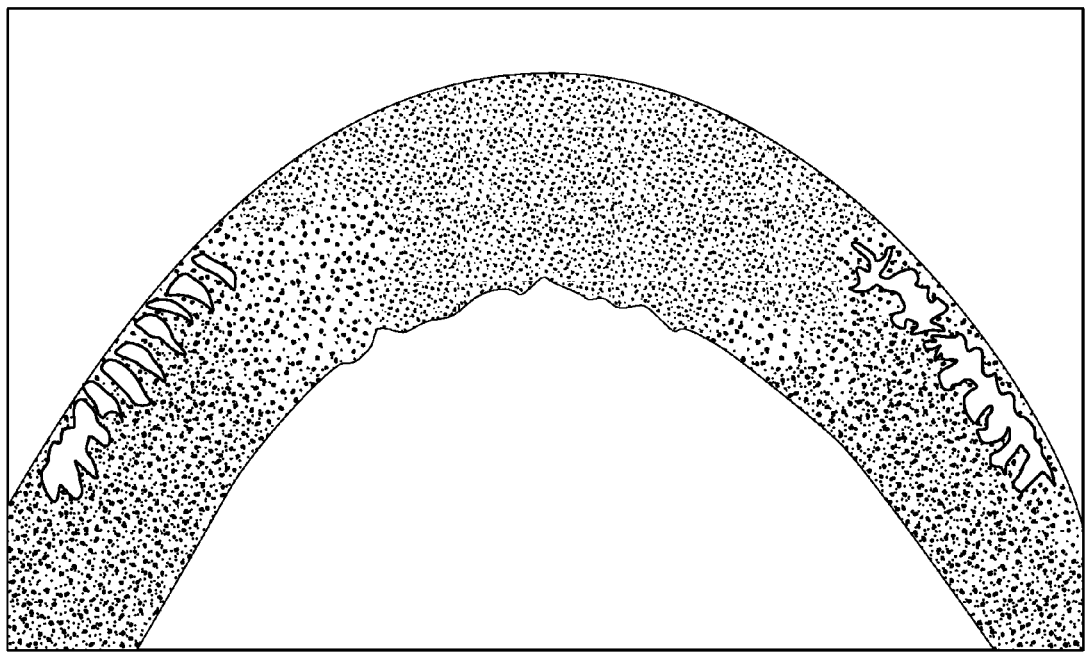
FIG. 14 is an OCT image illustrating an intrastromal incision pattern in accordance with another embodiment.

FIGS. 9-14 are optical coherence tomography (OCT) images illustrating a variety of intrastromal incision patterns formed in a cornea. In FIGS. 9 and 10, the intrastromal incision pattern includes incisions at 30° (e.g., based on the corneal layer being at horizontal). In FIG. 12, the intrastromal incision pattern includes incisions at 120°. In FIG. 13, the intrastromal incision pattern includes incisions at 45°. In FIG. 14, the intrastromal incision pattern includes incisions Thus, systems 10, 30 and methods for intrastromal refractive correction are disclosed. The systems 10, 30 can be used to form a variety of intrastromal incision patterns, including but not necessarily limited to, the patterns illustrated in FIGS. 3-14. Additionally, the systems and methods are suited to provide a desired post-procedure corneal re-shaping while preserving the corneal surface (e.g., the epithelium). Examples of some refractive correction applications for the system 10, 30 include, but are not necessarily limited to, presbyopia, myopia, astigmatism related conditions, or the like.

While embodiments of this invention have been shown and described, it will be apparent to those skilled in the art that many more modifications are possible without departing from the inventive concepts herein.

What is claimed is:

1. A system for correcting the refractive condition of an eye having a cornea with an anterior surface and an endothelium, the system comprising:
  a laser subsystem operable to produce a non-ultraviolet, ultrashort pulsed beam in the range of 400 nm to 3000 nm;
  a patient interface configured to applanate the cornea during an intrastromal incision such that the patient interface is a planar surface, and the pulsed beam is directed through the patient interface and into the cornea;
  a scanner operable to direct the pulsed beam at the eye; and
  a controller coupled to the laser subsystem and the scanner, the controller configured to:
    determine an intrastromal incision pattern based on the refractive condition; and
    direct the scanner to intrastromally incise the pattern in the cornea with the pulsed beam through plasma mediated photodisruption, the refractive condition being corrected by the pattern intrastromally incised in the cornea following de-applanation of the cornea by the patient interface, wherein
    the pattern has a maximum radius of 5 mm, a minimum radius of 1 mm, a minimum depth from the anterior surface of the cornea of 50 microns, and a maximum depth of 50 microns toward the anterior surface from the endothelium of the cornea.

2. The system of claim 1, further comprising a controller configured to:
  determine an intrastromal incision pattern based on a correction of myopia; and
  direct the scanner to intrastromally incise the pattern in the cornea with the pulsed beam through plasma mediated photodisruption, the myopia being corrected by the pattern intrastromally incised in the cornea following de-applanation of the cornea by the patient interface.

3. The system of claim 2, wherein the controller is further configured to direct the scanner to intrastromally incise the pattern in the cornea with the pulsed beam through plasma mediated photodisruption, the cornea reshaping in response to the intrastromal pattern incised in the cornea to correct for myopia.

4. The system of claim 1, further comprising a controller coupled to the laser subsystem and the scanner, the controller configured to:
   determine an intrastromal incision pattern based on myopia; and
   direct the scanner to intrastromally incise the pattern in the cornea with the pulsed beam through plasma mediated photodisruption, the myopia being corrected by the pattern intrastromally incised in the cornea following de-applanation of the cornea by the patient interface, wherein
   the pattern is configured to reshape the cornea; and
   the pattern has a maximum radius of 5 mm, a minimum radius of 1 mm, a minimum depth from the anterior surface of the cornea of 50 microns, and a maximum depth of 50 microns toward the anterior surface from the endothelium of the cornea.

5. The system of claim 1, wherein the pattern comprises a plurality of spots, each spot of the plurality of spots associated with a pulse beam energy of 0.01 µJ to 1 µJ.

6. The system of claim 1, wherein the intrastromal incision pattern comprises a plurality of intrastromal incisions radially oriented about an optical axis of the eye, each incision of the plurality of intrastromal incisions extending between an inner radius of the optical axis and an outer radius of the optical axis.

7. The system of claim 6, wherein the inner radius is 6 mm, the outer radius is 9.5 mm, and the plurality of intrastromal incisions comprises 32 intrastromal incisions.

8. The system of claim 6, wherein at least one incision of the plurality of intrastromal incisions has a zig-zag cross-section.

* * * * *